(12) United States Patent
Schubert et al.

(10) Patent No.: US 10,054,588 B2
(45) Date of Patent: Aug. 21, 2018

(54) MARKERS FOR DETERMINATION OF PATIENT RESPONSIVENESS

(71) Applicant: The Board of Trustees of the Leland Stanford Junior University, Stanford, CA (US)

(72) Inventors: Ryan D. Schubert, San Francisco, CA (US); Robert C. Axtell, Oklahoma City, OK (US); Jeffrey Edward Dunn, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 205 days.

(21) Appl. No.: 14/781,885

(22) PCT Filed: Apr. 4, 2014

(86) PCT No.: PCT/US2014/033057
§ 371 (c)(1),
(2) Date: Oct. 1, 2015

(87) PCT Pub. No.: WO2014/165812
PCT Pub. Date: Oct. 9, 2014

(65) Prior Publication Data
US 2016/0054320 A1 Feb. 25, 2016

Related U.S. Application Data

(60) Provisional application No. 61/808,528, filed on Apr. 4, 2013.

(51) Int. Cl.
*G01N 15/14* (2006.01)
*A61K 31/785* (2006.01)
(Continued)

(52) U.S. Cl.
CPC ..... *G01N 33/56972* (2013.01); *A61K 31/785* (2013.01); *A61K 38/215* (2013.01);
(Continued)

(58) Field of Classification Search
CPC ............. G01N 33/56972; G01N 15/14; G01N 33/5052; G01N 2015/1486;
(Continued)

(56) References Cited

U.S. PATENT DOCUMENTS

| 8,021,840 B2 | 9/2011 | Bhan et al. | |
| 2003/0017136 A1* | 1/2003 | Cruz | A61K 31/714 424/85.6 |
| 2010/0304996 A1* | 12/2010 | Seyfert | C12Q 1/6883 506/9 |

OTHER PUBLICATIONS

Gandhi et al. BAFF is a Biological Response Marker to IFN-β Treatment in Multiple Sclerosis. Journal of Interferon & Cytokine Research 28: 529-540 (2008).*

(Continued)

*Primary Examiner* — Gailene Gabel
(74) *Attorney, Agent, or Firm* — Pamela J. Sherwood; Bozicevic, Field & Francis LLP

(57) ABSTRACT

Compositions and methods are provided for classification of individuals suffering from a demyelinating disease into groups that are informative of the individual's responsiveness or lack of responsiveness to treatment with a β-interferon (IFNβ) acting therapy. In particular, it is shown that the effective immunomodulatory treatment of demyelinating disease with IFNβ is associated with an increase in circulating transitional B cells in the patient. Diseases of interest include without limitation inflammatory demyelinating diseases of the central nervous system, e.g. multiple sclerosis, neuromyelitis optica (NMO), experimental autoimmune encephalitis (EAE), acute disseminated encephalomyelitis (ADEM), etc.

8 Claims, 8 Drawing Sheets

(51) Int. Cl.
  *G01N 33/569* (2006.01)
  *G01N 33/50* (2006.01)
  *A61K 38/21* (2006.01)
  *G01N 15/10* (2006.01)

(52) U.S. Cl.
  CPC ......... *G01N 15/14* (2013.01); *G01N 33/5052* (2013.01); *G01N 2015/1006* (2013.01); *G01N 2015/1486* (2013.01); *G01N 2333/525* (2013.01); *G01N 2333/565* (2013.01); *G01N 2469/10* (2013.01); *G01N 2800/285* (2013.01); *G01N 2800/52* (2013.01)

(58) Field of Classification Search
  CPC ....... G01N 2333/525; G01N 2333/565; G01N 2469/10; G01N 2015/1006; G01N 2800/52; G01N 2800/285; A61K 31/785; A61K 38/215
  See application file for complete search history.

(56) References Cited

OTHER PUBLICATIONS

Gandhi et al. "BAFF Is a Biological Response Marker to IFN-β Treatment in Multiple Sclerosis," Journal of Interferon & Cytokine Research, Aug. 21, 2008 (Aug. 21, 2008), vol. 28, Iss. 09, pp. 529-540.

Rowland et al. "BAFF-R signaling aids the differentiation of immature B cells 1-10 into transitional B cells following tonic BCR signaling," The Journal of Immunology, Oct. 15, 2010 (Oct. 15, 2010), vol. 185, Iss. 08, pp. 4570-4581.

\* cited by examiner

MARKERS FOR DETERMINATION OF PATIENT RESPONSIVENESS

BACKGROUND

There is a long-standing interest in manipulating cells of the immune system to achieve control of autoimmune disease. While targeted antigen-specific therapy remains of great interest, there has also been considerable development of polyclonal, or non-antigen specific therapies. In addition to general immunosuppression, e.g. through the use of agents such as hydrocortisone, many therapies are now being brought to the clinic that provide for a more selective modification of the immune system, such as modulation of cytokines.

Multiple sclerosis (MS) is the most common autoimmune illness of the central nervous system. For many years the inflammatory manifestations of MS were treated using only corticosteroids. However, more recently the results of clinical trials with immunomodulatory agents have changed the therapeutic approach to this disease. Interferon beta (IFNβ)-1b represents the pioneer of those therapies. There is growing evidence from clinical trials on relapsing-remitting MS and clinically isolated syndromes suggestive of MS that IFNβ-1b reduces the frequency and severity of relapses and the development of new and active brain lesions. There can be a significant benefit to treatment early in the disease, for example as shown by the Betaferon/Betaseron in Newly Emerging Multiple Sclerosis For Initial Treatment (BENEFIT) study. Irreversible axonal damage can begin early in the course of MS, and immunomodulatory treatment of MS can have a greater effect early in the disease course.

A downside to this promising therapy is the diversity of responses in patient populations. While a significant proportion of patients can respond to a particular therapy, many do not. The clinician can therefore need to prescribe sequential expensive and time-consuming therapies in order to determine which is effective for the individual patient. Furthermore, it has been reported that IFN-β can exacerbate symptoms in some individuals.

The use of disease-modifying therapies in autoimmune conditions is of great clinical interest; however these therapies suffer from the inability to determine using a blood test whether a patient's immune system is responding appropriately to treatment. The present invention addresses this need.

Publications of interest include Ramgolam et al. (2011) J Immunol. 186(7):4518-26, entitled "B cells as a therapeutic target for IFN-β in relapsing-remitting multiple sclerosis"; Meinl et al. (2011) J Neurol Sci. 306(1-2):180-2, entitled 'Humoral autoimmunity in multiple sclerosis'; Krumbholz et al. (2008) Brain 131(Pt 6):1455-63, entitled 'Interferon-beta increases BAFF levels in multiple sclerosis: implications for B cell autoimmunity'; Quan et al. (2012) Mult. Sclerosis, entitled 'Impaired regulatory function and enhanced intrathecal activation of B cells in neuromyelitis optica: distinct from multiple sclerosis'; and Thangarajh et al. (2007) Scand J Immunol. 65(5):461-6, entitled 'The expression of BAFF-binding receptors is not altered in multiple sclerosis or myasthenia gravis'.

SUMMARY

Compositions and methods are provided for classification of individuals suffering from a demyelinating disease into groups that are informative of the individual's responsiveness or lack of responsiveness to treatment with a β-interferon (IFNβ) acting therapy. In particular, it is shown that the effective immunomodulatory treatment of demyelinating disease with IFNβ is associated with an increase in circulating transitional B cells in the patient. Diseases of interest include without limitation inflammatory demyelinating diseases of the central nervous system, e.g. multiple sclerosis, neuromyelitis optica (NMO), experimental autoimmune encephalitis (EAE), acute disseminated encephalomyelitis (ADEM), etc.

In some embodiments, a method is provided for determining if a patient is responsive to an IFNβ agent. In the methods of the invention, a sample comprising lymphocytes, which is drawn conveniently from the peripheral blood, although other hematopoietic cell samples may also find use, of a patient undergoing treatment with an IFNβ agent, is analyzed for transitional B cell content. Patients responsive to the IFNβ therapy have an increase in transitional B cells relative to the level prior to treatment or compared to an untreated healthy control individual. The increase may be measured on an absolute level, as a percentage of total peripheral blood mononuclear cells (PBMC), as a percent to B cells, e.g. a percent of $CD19^+$ PBMC, etc. The increase may be measured relative to a healthy control, relative to the same patient prior to therapy, relative to predetermined standard, and the like. Determination of transitional B cell counts may be performed by ELISA, flow cytometry, microscopy, etc., as is known in the art. Various markers are useful in distinguishing transitional B cells from mature B cells or pre-B cells, including, without limitation, the markers CD19, CD20, CD21, CD22, CD23, CD24, CD38, IgD, IgM, AA4.1, etc. Transitional B cells can be broadly characterized as $CD19^+CD20_+$, which are markers for B cells generally, $CD24^{hi}CD38^{hi}$, which together label transitional cells, $IgD^+$ and/or $IgM^+$ which respectively subset transitional B cells into Type 2 and Type 1 transitional B cells.

Assessment of responsiveness in a patient allows improved care and monitoring, where patients classified as responsive to an IFNβ agent can be treated with such an agent, while a patient that is not responding can be moved to an alternative treatment. For example, β-IFN and similar drugs can be advised or provided for patients classified as responsive, while patients classified as a predominantly non-responsive can be treated with other available agents, e.g. copaxone, fingolimod, natalizumab, dimethyl fumarate, teriflunomoide, etc. Patients can be classified upon initial treatment of symptoms, and can be further monitored for clinical status and transitional b cell level over the course of the disease to maintain appropriate therapy, or can be classified at any appropriate stage of disease progression. In one embodiment, the method further comprises selecting a therapeutic regimen based on the analysis and treating the patient accordingly. In an embodiment, the method further comprises determining a treatment course for the subject based on the analysis. In some embodiments an assessment of the patient responsiveness is provided to the patient or health care provider.

In other embodiments of the invention a device or kit is provided for the analysis of patient samples. Such devices or kits will include reagents that are useful in the characterization of transitional B cells, e.g. reagents that specifically bind to one or more of CD19, CD20, CD21, CD22, CD23, CD24, CD38, IgD, IgM, AA4.1, etc. The reagents can be provided as a kit comprising reagents in a suspension or suspendable form, e.g. detectably labeled reagents suitable for flow cytometry, and the like.

BRIEF DESCRIPTION OF THE DRAWINGS

FIG. 6A shows profiles of CD19+IgD low or high B cells after treatment with IFNβ. Shown in FIG. 6B are changes in T1, T2, marginal zone and follicular B cells following treatment with IFNβ.

Figure 1:
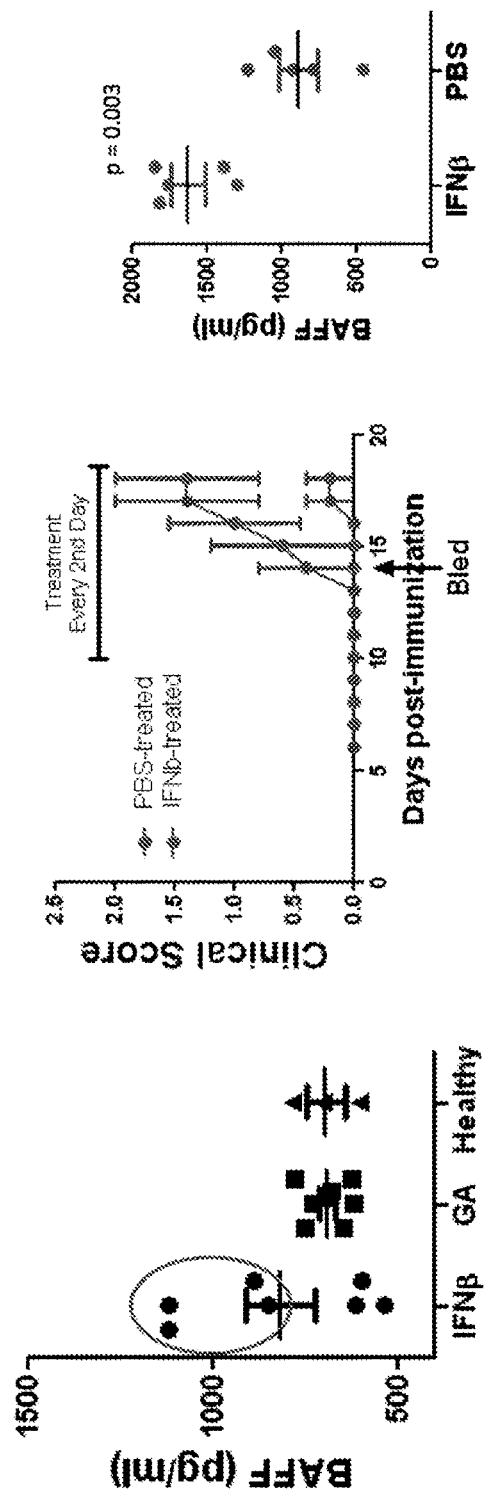
FIG. 1. B-cell activation factor (BAFF) is elevated in IFNβ treated MS and EAE.
Figure 2:
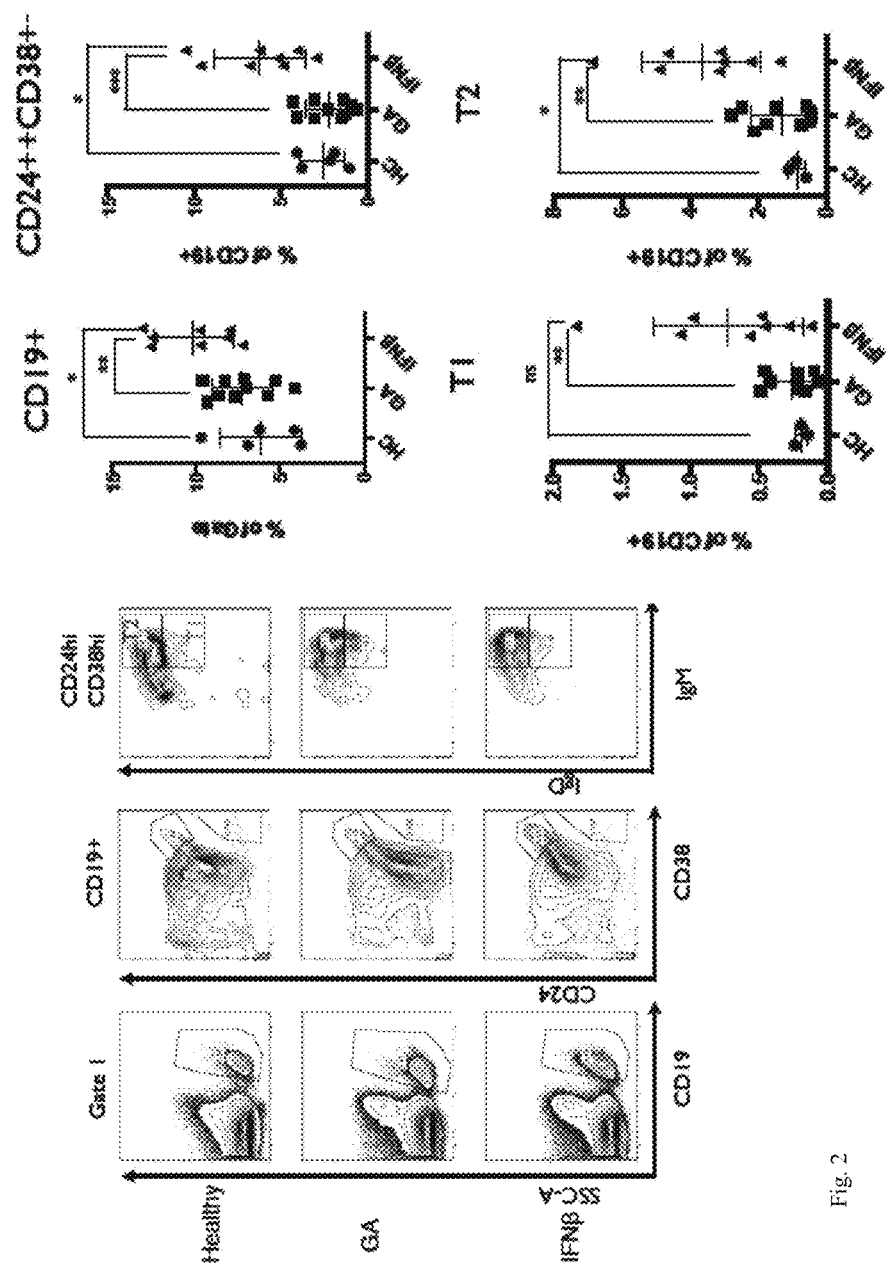
FIG. 2. Transitional B cell expansion is a signature of IFNβ therapy in MS. Patient samples were immediately processed for mononuclear cell isolation at the time of collection. These cells were cryopreserved and then thawed for flow cytometry. Statistical significance was determined using Student's unpaired t-test with *p<0.05 and **p<0.005.
Figure 3:
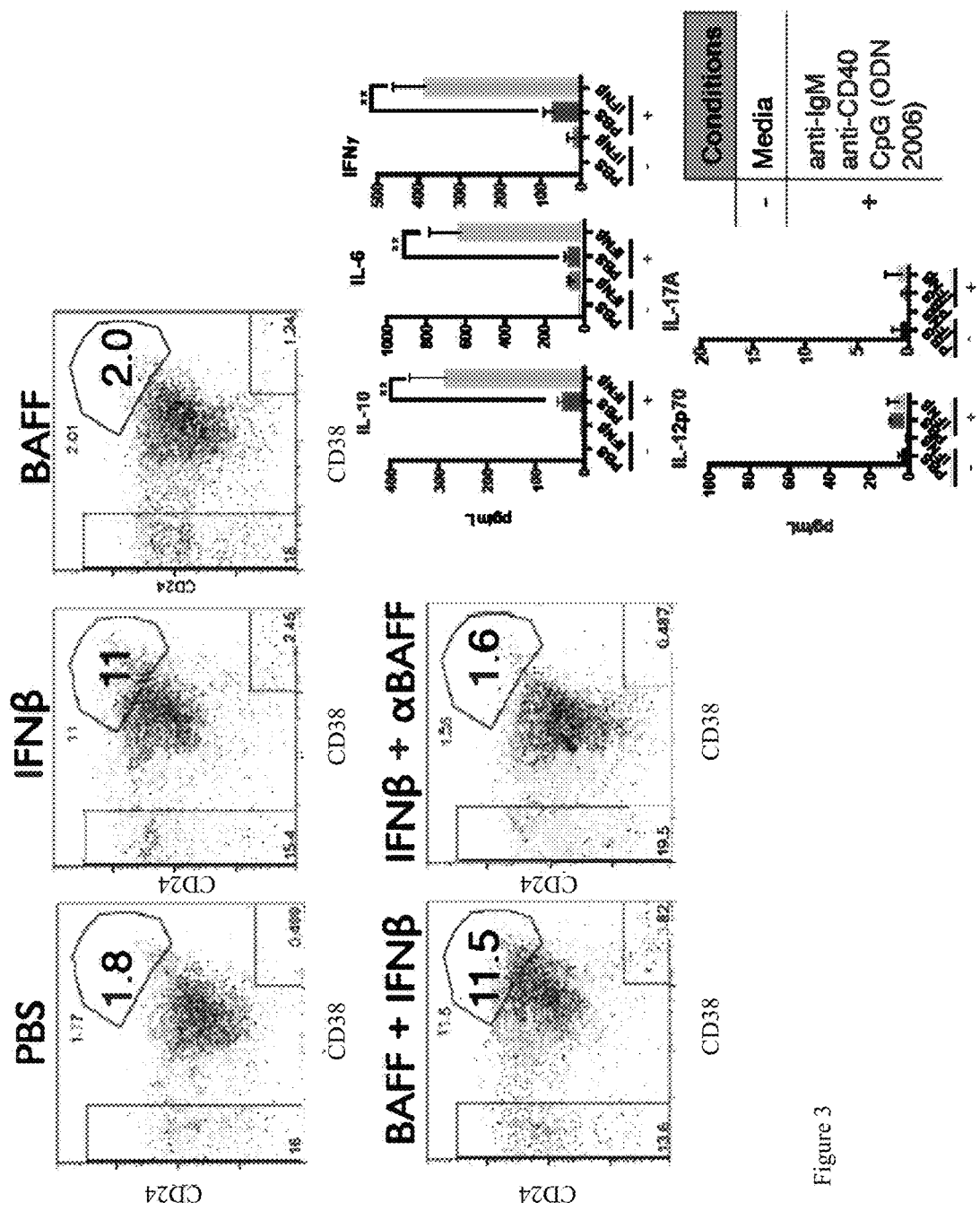
FIG. 3. IFNβ's effect on B cells requires BAFF and stimulates IL-10, IL-6, and IFNγ production. (Left) PBMCs from a healthy human volunteer were stimulated with the indicated reagent(s) for 24 hours and then analyzed by flow cytometry. Shown after gating for $CD19_+$ cells. Numbers indicate percentage of events falling in the indicated gate. (Right) PBMCs from 7 healthy human volunteers were stimulated in vitro with the indicated conditions. Cytokine levels in culture supernatants were determined using ELISA. Statistical significance was done with paired Student's t-test *p<0.05 and **p<0.005.
Figure 4:
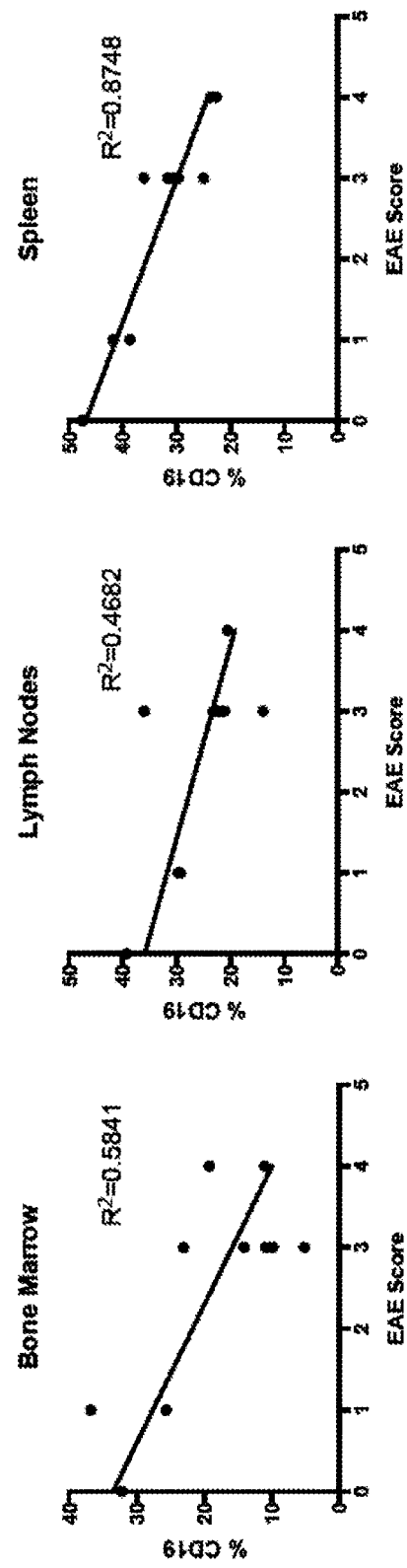
FIG. 4. EAE severity inversely correlates the number of B cells.
Figure 5:
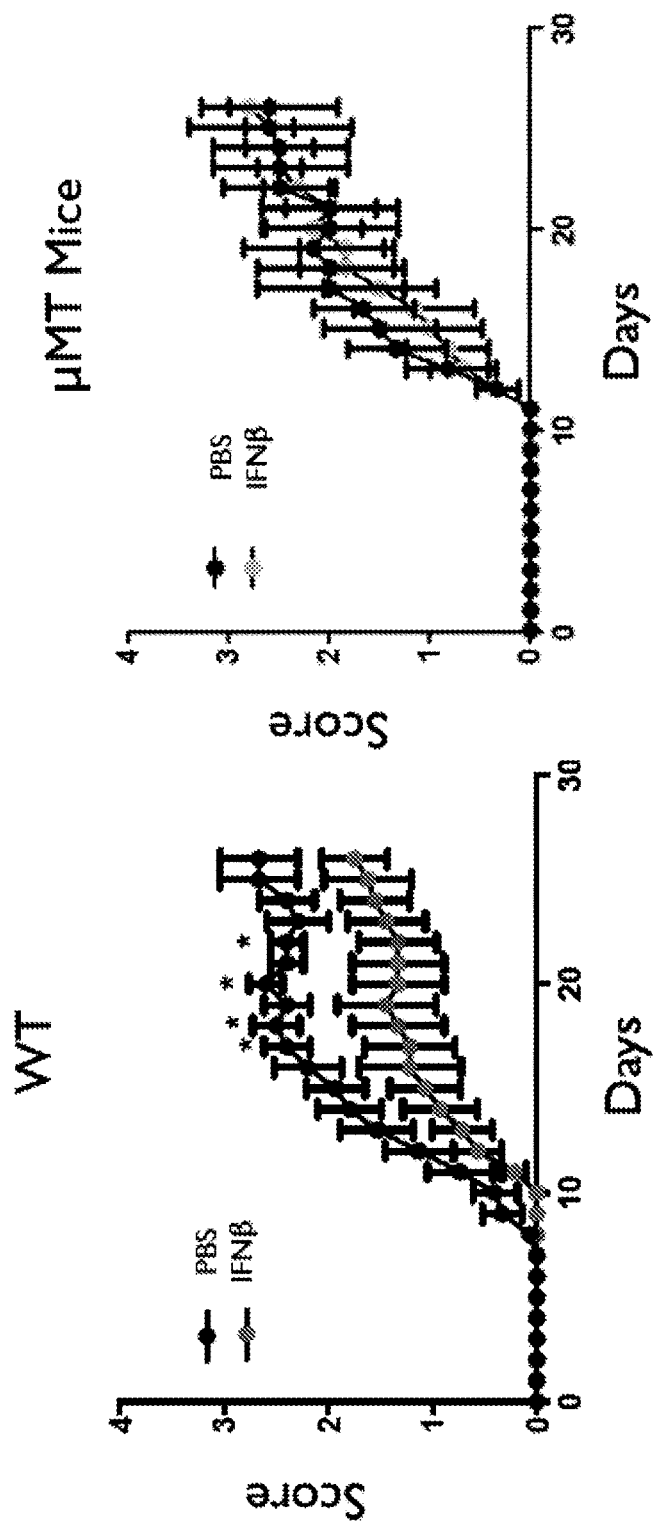
FIG. 5. μMT mice are B cell deficient and fail IFNβ therapy in EAE. EAE was induced in healthy female C57/B6 mice via subcutaneous immunization with 100 μg $MOG_{35-55}$ in an emulsion with complete Freund's adjuvant (CFA, Difco). Mice were also injected i.p. with 400 ng Bordetella pertussis toxin (List Biological Laboratories) at the time of and two days after immunization. Beginning at day 6, mice received injections every other day with either phosphate buffered saline or recombinant mouse interferon-B (R&D systems). The μMT mouse (Jackson Labs) does not express IgM and lacks mature B cells. Significance was determined using an unpaired Student's t-test at each day, with *p<0.05.
Figure 6A:
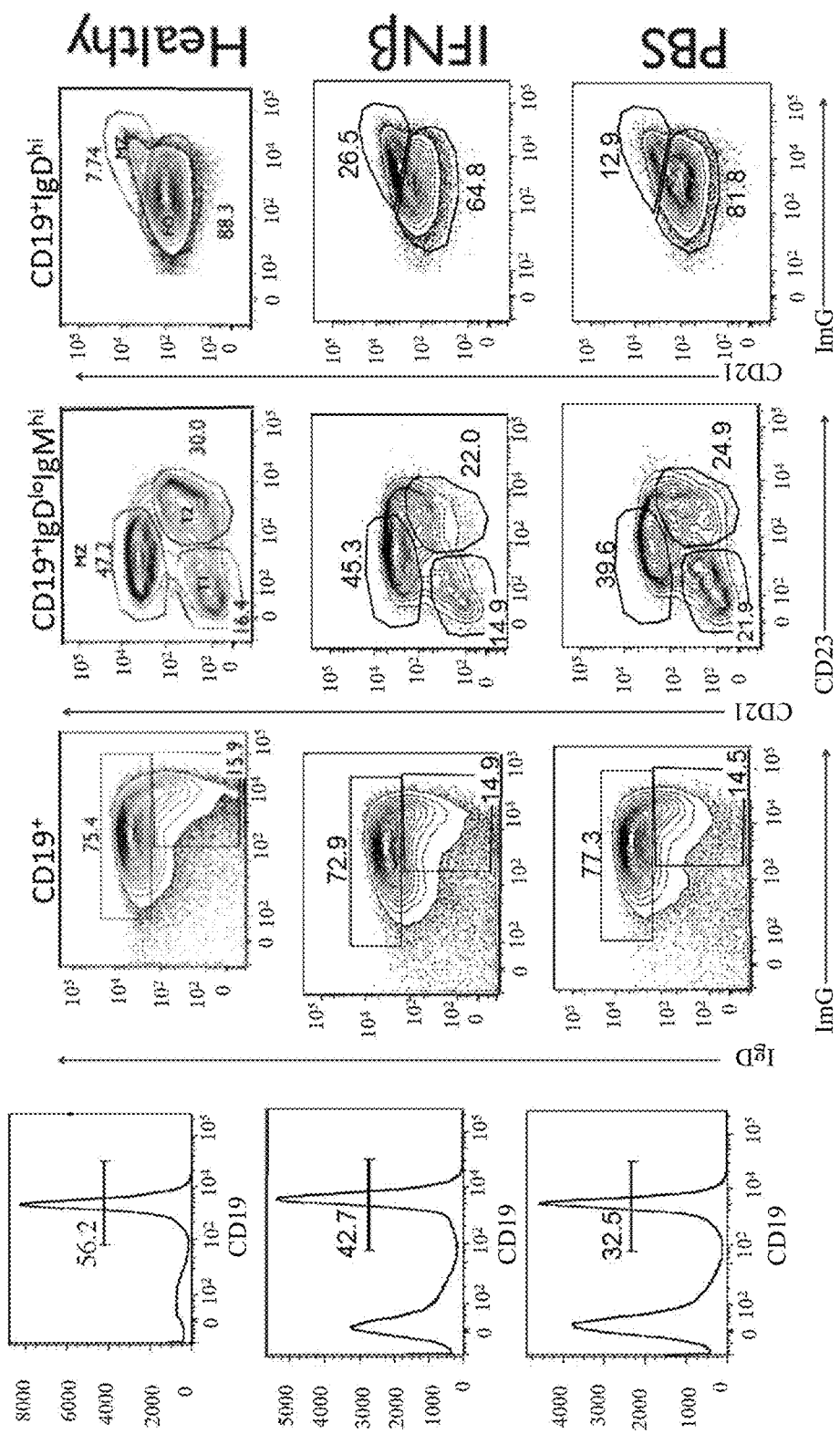
FIG. 6A-B.
Figure 6B:
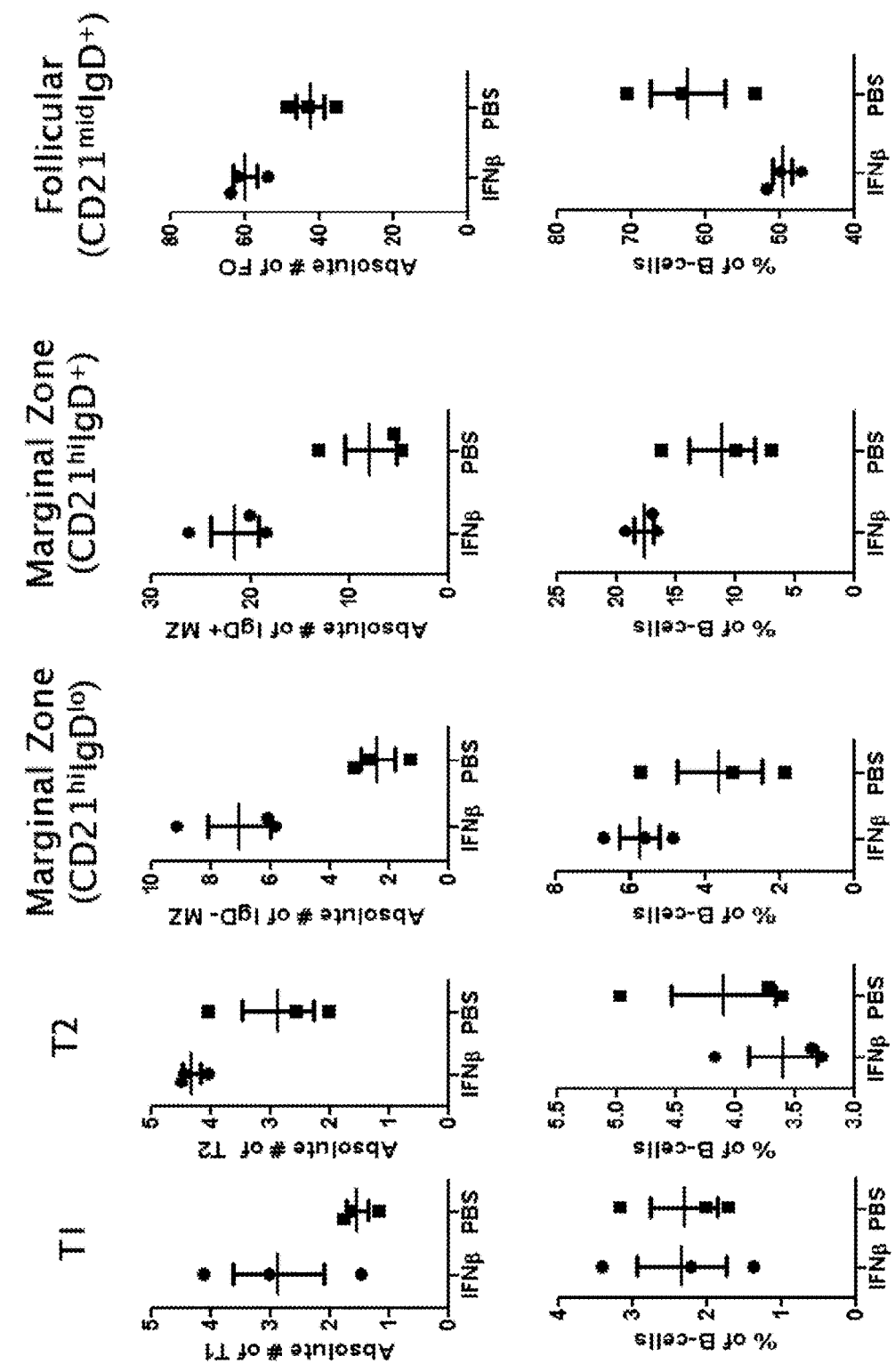
Figure 7:
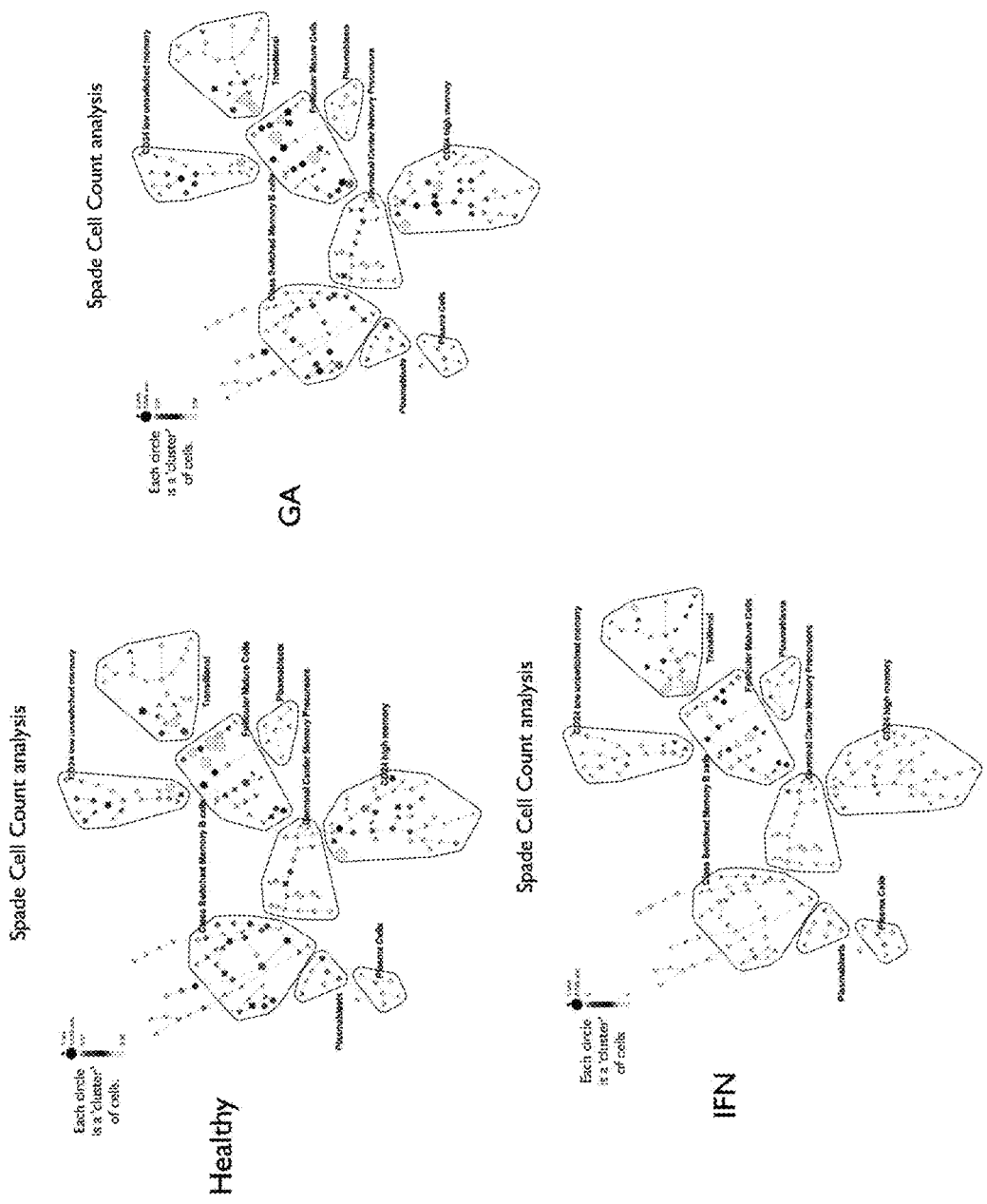
FIG. 7. A Spade cell count analysis using the makers CD19, CD24, CD38, IgD, and IgM showing the distribution of B cell populations for a healthy control, and MS patients treated with copaxone (GA) or interferon beta (IFNβ).

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

It must be noted that, as used in the specification and the appended claims, the singular forms "a," "an," and "the" include plural referents unless the context clearly dictates otherwise.

DETAILED DESCRIPTION OF THE EMBODIMENTS

As exemplified herein by analysis of response of patient groups to IFNβ; there is a differential involvement of B cells in the effective treatment of demyelinating disease. Surprisingly, it is shown herein that an increase in transitional B cell populations is associated with the effective treatment of inflammatory demyelinating disease with IFNβ. Monitoring transitional B cell populations allows the classification of individuals being treated for responsiveness. Biomarkers that indicate the presence of transitional B cells are identified herein as indicative of responsiveness to IFNβ therapy.

The information obtained from the transitional B cell profile is used to (a) determine type and level of therapeutic intervention warranted (i.e. more versus less aggressive therapy, monotherapy versus combination therapy, type of combination therapy)), and (b) to optimize the selection of therapeutic agents. With this approach, therapeutic regimens can be individualized and tailored according to the response data obtained at different times over the course of treatment, thereby providing a regimen that is individually appropriate. In addition, patient samples can be obtained at any point during the treatment process for analysis.

Mammalian species that provide samples for analysis include canines; felines; equines; bovines; ovines; etc. and primates, particularly humans. Animal models, particularly small mammals, e.g. murine, lagomorpha, etc. can be used for experimental investigations. Animal models of interest include those for models of autoimmunity, graft rejection, and the like.

Definitions

Transitional B-cells. As used herein, the term is used to describe immature B-cells, which can be distinguished from mature B-cells by variations in cell surface markers, antigenic specificity, relative responsiveness to B-cell receptor signals, TLR receptor signaling, and other coreceptors, as well as cytokine production. Unique combinations of markers allow discrimination of different stages of development. The most immature transitional B-cells and recent emigrants from the bone marrow are called T1 B-cells (transitional type 1 B-cells or T1 cells). Others are T2 B-cells (transitional type 2 or T2 cells).

In humans, transitional $CD19^+$, $CD21^-$, $CD23^-$ B cells are $CD10^-$, $CD38^{hi}$, $CD24^{hi}$ and $CD44^{lo}$. $CD38^{hi}$ transitional B cells express variable amounts of CD20 and IgM. Essentially all $CD20^{hi}$, $CD38^{hi}$ B cells express both IgM and IgD, indicating that these cells have completed bone marrow maturation. The more mature population of $CD19^+$ $CD38^{neg/lo}$ bone marrow B cells are $CD20^+$, $IgM^+$, and $IgD^+$. The phenotype of $IgD^+CD38^{hi}$ transitional B cells in peripheral blood is consistent with expression of markers found on immature B cells from bone marrow and cord blood; they are $CD10^+$, $CD44^{lo}$, and $CD24^{hi}$ relative to mature naive B cells. These immature B cells are also $CD21^{lo}$, $CD23^{lo}$, $IgM^{hi}$, and $CD62L^{lo}$, a phenotype that is consistent with mouse transitional type 1 (T1) B cells. Relative to naive B cells, these T1 B cells express lower levels of CD40, CD22, CD124, and BR3. They are also negative or express a low density of CD27, CD77, CD80, CD86, CD69, CD11b, CD95, TACI, and BCMA, and a moderate density of CD19, B220, and CD32. These cells also express increased densities of CD20, CD5, CD43, and CD9 relative to naive B cells, and kappa or lambda light chains.

For the purposes of the present invention, any suitable combination of markers that identifies transitional B cells may be used, including, for example, $CD19^+CD38^+$ cells; $CD38^+IgD^+$ cells; $CD20^{hi}CD38^{hi}$ cells, and the like.

Inflammatory Disease. Inflammation is a process whereby the immune system responds to infection or tissue damage. Inflammatory disease results from an activation of the immune system that causes illness, in the absence of infection or tissue damage, or at a response level that causes illness. Inflammatory disease includes autoimmune disease, which are any disease caused by immunity that becomes misdirected at healthy cells and/or tissues of the body. Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease. Autoimmune diseases include diseases that affect specific tissues as well as diseases that can affect multiple tissues, which can depend, in part on whether the responses are directed to an antigen confined to a particular tissue or to an antigen that is widely distributed in the body.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity). A cell critical in mediating and regulating these effector functions are $CD4^+T$ cells, which can be subtyped as TH1, TH2, TH17, etc.

Demyelinating disease. Demyelinating disease may be characterized according to the presence of autoantibodies specific for lipids associated with the nervous system, and in particular with myelin. Myelin sheaths, which cover many nerve fibers, are composed of lipoprotein layers formed in early life. Myelin formed by the oligodendroglia in the CNS differs chemically and immunologically from that formed by the Schwann cells peripherally, but both types have the same function: to promote transmission of a neural impulse along an axon. Demyelinating diseases include those that affect the central nervous system, and those that affect the peripheral nervous system. CNS conditions include multiple sclerosis, acute disseminated encephalomyelitis (ADEM), neuromyelitis optica (NMO), and the animal model EAE, which are progressive CNS diseases characterized by disseminated patches of demyelination, resulting in multiple and varied neurologic symptoms and signs, usually with remissions and exacerbations.

Plaques of demyelination, with destruction of oligodendroglia and perivascular inflammation, are disseminated throughout the CNS, primarily in the white matter, with a predilection for the lateral and posterior columns (especially in the cervical and dorsal regions), the optic nerves, and periventricular areas. Tracts in the midbrain, pons, and cerebellum are also affected as is gray matter in the cerebrum and spinal cord. Cell bodies and axons are usually preserved, especially in recent lesions. Later, axons may be destroyed, especially in the long tracts, and a fibrous gliosis makes the tracts appear sclerotic. Recent and old lesions may coexist. Chemical changes in lipid and protein constituents of myelin occur in and around the plaques.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RRMS) is characterized clinically by relapses and remissions that occur over months to years, with partial or full recovery of neurological deficits between attacks. Such patients manifest approximately 1 attack, or relapse, pre year. Over 10 to 20 years, approximately 50% of RRMS patients develop secondary progressive MS (SPMS) which is characterized by incomplete recovery between attacks and accumulation of neurologic deficits resulting in increasing disability.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, may show plaques. It may also detect treatable nondemyelinating lesions at the junction of the spinal cord and medulla (eg, subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions may also be visible on contrast-enhanced CT scans; sensitivity may be increased by giving twice the iodine dose and delaying scanning (double-dose delayed CT scan).

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Conventional treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Neuromyelitis optica (NMO), or Devic's disease, is an autoimmune, inflammatory disorder of the optic nerves and spinal cord. Although inflammation may affect the brain, the disorder is distinct from multiple sclerosis, having a different pattern of response to therapy, possibly a different pattern of autoantigens and involvement of different lymphocyte subsets.

The main symptoms of Devic's disease are loss of vision and spinal cord function. As for other etiologies of optic neuritis, the visual impairment usually manifests as decreased visual acuity, although visual field defects, or loss of color vision may occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelinization), but they differ from MS pattern II lesions in their prominent perivascular distribution. Therefore, the pattern of inflammation is often quite distinct from that seen in MS.

Attacks are conventionally treated with short courses of high dosage intravenous corticosteroids such as methylprednisolone IV. When attacks progress or do not respond to corticosteroid treatment, plasmapheresis may be used. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study.

The disease can be monophasic, i.e. a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike MS, Devic's disease rarely has a secondary progressive phase in which patients have increasing neurologic decline between attacks without remission. Instead, disabilities arise from the acute attacks.

Acute disseminated encephalomyelitis (ADEM) is an immune mediated disease of the brain that can occur spontaneously, or following a viral infection, vaccination, bacterial or parasitic infection. It is considered part of the Multiple sclerosis borderline diseases. The incidence rate is about 8 per 1,000,000 people per year. Although it occurs in all ages, most reported cases are in children and adolescents, with the average age around 5 to 8 years old. The mortality rate may be as high as 5%, full recovery is seen in 50 to 75% of cases, while up to 70 to 90% recover with some minor residual disability. The average time to recover is one to six months.

ADEM produces multiple inflammatory lesions in the brain and spinal cord, particularly in the white matter, i.e. demyelination. Usually these are found in the subcortical and central white matter and cortical gray-white junction of both cerebral hemispheres, cerebellum, brainstem, and spinal cord, but periventricular white matter and gray matter of the cortex, thalami and basal ganglia may also be involved.

When the patient suffers more than one demyelinating episode, it may be referred to as recurrent disseminated encephalomyelitis or multiphasic disseminated encephalomyelitis (MDEM). Acute hemorrhagic leukoencephalitis (AHL, or AHLE), also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease, is a hyperacute and frequently fatal form of ADEM, and is characterized by necrotizing vasculitis of venules and hemorrhage, and edema. Death is common in the first week and overall mortality is about 70%, but increasing evidence points to favorable outcomes after aggressive treatment with corticosteroids, immunoglobulins, cyclophosphamide, and plasma exchange.

Peripheral neuropathies include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Interferon beta-1a/b are drugs in the interferon family used to treat multiple sclerosis (MS). Interferon beta-1a is manufactured using mammalian cells while Interferon beta-1b is produced in modified *E. coli*. Interferons have been shown to have about a 18-38% reduction in the rate of MS relapses, and to slow the progression of disability in MS patients. Commercially available products include Avonex (Biogen Idec); Rebif (EMD Serono); and CinnoVex (CinnaGen). Closely related is Interferon beta-1b, which is marketed in the US as Betaseron, or Extavia. β-IFN find use in the treatment of patients classified by the methods of the invention as responsive to β-interferon.

Copaxone, manufactured by Teva Marion Partners, is the brand name for a synthetic chemical used to modify the course of multiple sclerosis. The generic name of Copaxone is Glatiramer Acetate which is often shortened to GA. In early trials of the drug, it was known as Copolymer-1 and Cop-1. Copaxone is a random chain of amino acids—Glutamic acid, Lysine, Alanine and Tyrosine (hence GLATiramer). It is synthesized in solution from these amino acids a ratio of approximately 5 parts alanine to 3 of lysine, 1.5 of glutamic acid and 1 of tyrosine using N-carboxyamino acid anhydrides.

Copaxone has been shown in clinical trials to reduce the average relapse rate in people with the relapsing-remitting (RRMS) form of the disease. Copaxone has also been shown to limit the formation of new MS-related lesions in the central nervous system and to reduce brain atrophy. Copaxone finds use in the treatment of patients classified by the methods of the invention as unresponsive to β-interferon.

Statins are inhibitors of HMG-CoA reductase enzyme. These agents are described in detail, for example, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171; fluvastatin and related compounds as disclosed in U.S. Pat. No. 5,354,772; atorvastatin and related compounds as disclosed in U.S. Pat. Nos. 4,681,893, 5,273,995 and 5,969,156; and cerivastatin and related compounds as disclosed in U.S. Pat. Nos. 5,006,530 and 5,177,080. Additional compounds are disclosed in U.S. Pat. Nos. 5,208,258, 5,130,306, 5,116,870, 5,049,696, RE 36,481, and RE 36,520. Statins include the salts and/or ester thereof. Specific examples of statins include atorvastatin (LIPITOR™); cerivastatin (LIPOBAY™); fluvastatin (LESCOL™); lovastatin (MEVACOR™); mevastatin (COMPACTIN™); pitavastatin (LIVALO™); pravastatin (PRAVACHOL™); Rosuvastatin (CRESTOR™); simvastatin (ZOCOR™); etc.

Simvastatin, the lipid-lowering drug first marketed as Zocor, has been investigated for use in multiple sclerosis, and shown to inhibit Th17 cell differentiation in patients with relapsing-remitting multiple sclerosis. Experiments suggest that simvastatin alters $CD45RA_+$ cells undergoing Th17 differentiation. Simvastatin and other statins find use in the treatment of patients that are unresponsive to β-interferon.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response. An "immunogen" is capable of inducing an immunological response against itself on administration to a mammal or due to autoimmune disease.

A "subject" or "patient" in the context of the present teachings is generally a mammal. Mammals other than humans can be advantageously used as subjects that represent animal models of inflammation. A subject can be male or female.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis to, e.g., determine whether a subject is a responder or a non-responder to a therapy (e.g., an IFN treatment as described herein).

A "sample" in the context of the present teachings refers to any biological sample that is isolated from a subject, generally a sample that comprises leukocytes. A sample can include, without limitation, an aliquot of body fluid, whole blood, white blood cells or leucocytes, synovial fluid, lymphatic fluid, cerebrospinal fluid, bone marrow, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or a fraction thereof, particularly peripheral blood mononuclear cells (PBMC), i.e. white blood cells or leucocytes. Samples can be obtained from a subject by any convenient means, as is known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring, cell counts by microscopy, flow cytometry, and the like. The phrase also encompasses receiving a set of data, e.g., from a third party that has processed the sample to experimentally determine the dataset. Additionally, the phrase encompasses mining data from at least one database or at least one publication or a combination of databases and publications.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUC or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC (area under the curve) of at least about 0.7, at least about 0.75, at least about 0.8, at least about 0.85, at least about 0.9, or higher.

As is known in the art, the relative sensitivity and specificity of a model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle &

Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of inflammatory disease can be accomplished by administration of the agent prior to development of a relapse. The treatment of ongoing disease, where the treatment stabilizes or improves the clinical symptoms of the patient, is of particular interest.

Methods

In one embodiment of the invention, a method is provided for determining whether a patient, e.g. an MS patient, is responding to IFNβ therapy. The determination can be made at an early time point after initiation of treatment, and can be made in the absence of other clinical disease indicia, thus providing an independent and sensitive means of monitoring responsiveness.

In the methods of the invention, a sample comprising lymphocytes is obtained from an individual, where the individual usually has been diagnosed with a demyelinating inflammatory disease, e.g. multiple sclerosis; and is or will be treated with an IFNβ drug. Time points prior to treatment are not indicative of responsiveness, but may be obtained as a baseline for comparison of post-treatment samples.

Samples can be obtained at a various time points following initiation of IFNβ treatment, e.g. at about 1, 2, 3, 4, 5, 6, 7 days, 1 week, 2 weeks, 3 weeks, 1 month, etc., and monitoring may be performed at regularly intervals as long as the patient is being treated.

The sample is analyzed for the presence of transitional B cells. Such analysis typically relies on detecting the presence of cells that have a specific combination of markers, which are conveniently although not exclusively, cell surface markers.

Analysis of the transitional B cell content of a sample may use any convenient method of counting cells. Analysis by cell staining may use conventional methods, as known in the art, including magnetic bead separation, affinity selection, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

In such methods, the cells in a sample are contacted with affinity reagents, e.g. antibodies, including derivatives thereof such as single chain, Fab fragments, etc. that specifically bind to markers of interest. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

For the purposes of the present invention, any suitable combination of markers that identified transitional B cells may be used, including, for example, $CD19^+CD24^{++}CD38^{++}$ cells; $CD38^+IgD^+$ cells; $CD20^{hi}CD38^{hi}$ cells, and the like. Other markers of interest include, without limitation, CD5, CD9, CD10, CD11b, CD19, CD20, CD21, CD22, CD23, CD24, CD27, CD38, CD40, CD43, CD44, CD69, CD77, CD80, CD86, CD95, CD124, and BR3, TACI, and BCMA.

Of particular interest is the use of antibodies as affinity reagents. Conveniently, these antibodies are conjugated with a label for use in analysis. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker. Antibodies need not be directly labeled but can be labeled with a second stage agent, e.g. antibody, avidin, etc.

The affinity reagents are added to cells, and incubated for a period of time sufficient to bind the available antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc. The cell sample is analyzed by any method that allows determination of cells having the phenotype of interest.

The number of transitional B cells may be read out as an absolute value, e.g. the number of transitional B cells per unit of blood, bone marrow, etc., where an increase in absolute number relative to an untreated or unresponsive control is determined.

Conveniently, the transitional B cell count can be determined as a percentage of total B cells, or as a percentage of total lymphocytes. The number of transitional B cells as a percent of total B cells, e.g. as a percent of $CD19_+$ cells from healthy control peripheral blood is usually less than about 3%. The percentage of transitional B cells as a percent of total B cells, e.g. as a percent of $CD19_+$ cells from individuals responsive to IFNβ treatment is usually greater than about 3%, greater than about 5%, greater than about 6%, greater than about 7%, and may be higher, e.g. greater than about 10%, than about 12%, than about 15%.

The detection reagents can be provided as part of a kit. Thus, the invention further provides kits for detecting the presence of a panel of specific markers to assess the number of transitional B cells in a biological sample. Procedures using these kits can be performed by clinical laboratories, experimental laboratories, medical practitioners, or private individuals. The kits of the invention for detecting markers comprise affinity reagents useful for identifying transitional B cells, which can be provided in solution or bound to a substrate. The kit can optionally provide additional components that are useful in the procedure, including, but not limited to, buffers, developing reagents, labels, reacting surfaces, means for detection, control samples, standards, instructions, and interpretive information.

In addition to the above components, the subject kits will further include instructions for practicing the subject methods. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that can be present is a website address which can be used via the internet to access the information at a removed site. Any convenient means can be present in the kits.

Clinical Trials

In some preferred embodiments, the methods of the invention are used in determining the efficacy of a therapy for treatment of an inflammatory demyelinating disease, either at an individual level, or in the analysis of a group of patients, e.g. in a clinical trial format. Such embodiments typically involve the comparison of two time points for a patient or group of patients. The patient status is expected to differ between the two time points as the result of a therapeutic agent, therapeutic regimen, or disease challenge to a patient undergoing treatment.

Examples of formats for such embodiments may include, without limitation, testing samples for the presence of B cells at two or more time points, where a first time point is a diagnosed but untreated patient; and a second or additional time point(s) is a patient treated with a candidate therapeutic agent or regimen, for example an agent that is an IFNβ or that mimics the physiological activity of an IFNβ agent.

In another format, a first time point is a diagnosed patient in disease remission, e.g. as ascertained by current clinical criteria, as a result of a candidate therapeutic agent or regimen. A second or additional time point(s) is a patient treated with a candidate therapeutic agent or regimen.

In such clinical trial formats, each set of time points may correspond to a single patient, to a patient group, e.g. a cohort group, or to a mixture of individual and group data. Additional control data may also be included in such clinical trial formats, e.g. a placebo group, a disease-free group, and the like, as are known in the art. Formats of interest include crossover studies, randomized, double-blind, placebo-controlled, parallel group trial is also capable of testing drug efficacy, and the like. See, for example, Clinical Trials: A Methodologic Perspective Second Edition, S. Piantadosi, Wiley-Interscience; 2005, ISBN-13: 978-0471727811; and Design and Analysis of Clinical Trials: Concepts and Methodologies, S. Chow and J. Liu, Wiley-Interscience; 2003; ISBN-13: 978-0471249856, each herein specifically incorporated by reference.

In one embodiment, a blinded crossover clinical trial format is utilized. A patient alternates for a set period of time, e.g. one week, two weeks, three weeks, or from around about 7-14 days, or around about 10 days, between a test drug and placebo, with a 4-8 week washout period.

Assessment of Patient Outcomes

Patient outcomes and responder status can be assessed using imaging-based criteria such as radiographic scores, clinical and laboratory criteria. Multiple different imaging, clinical and laboratory criteria and scoring systems have been and are being developed to assess disease activity and response to therapy in inflammatory diseases, including without limitation inflammatory demyelinating disease, e.g. multiple sclerosis, neuromyelitis optica, etc.

In order to identify profiles that are indicative of responsiveness, a statistical test will provide a confidence level for a change in the numbers of transitional B cells between the test and control profiles to be considered significant, where the control profile can be for responsiveness or non-responsiveness. The raw data can be initially analyzed by measuring the values for each marker, usually in duplicate, triplicate, quadruplicate or in 5-10 replicate features per marker.

A test dataset is considered to be different than a control dataset if one or more of the parameter values of the profile exceeds the limits that correspond to a predefined level of significance.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering can be performed, where the Pearson correlation is employed as the clustering metric. One approach is to consider a patient disease dataset as a "learning sample" in a problem of "supervised learning". CART is a standard in applications to medicine (Singer (1999) Recursive Partitioning in the Health Sciences, Springer), which can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that can be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

These tools and methods can be applied to several classification problems. For example, methods can be developed from the following comparisons: i) all cases versus all controls, ii) all cases versus nonresponsive controls, iii) all cases versus responsive controls.

In a second analytical approach, variables chosen in the cross-sectional analysis are separately employed as predictors. Given the specific outcome, the random lengths of time each patient will be observed, and selection of proteomic and other features, a parametric approach to analyzing responsiveness can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models can be used, especially since reductions of numbers of covariates to manageable size with the lasso will significantly simplify the analysis, allowing the possibility of an entirely nonparametric approach to survival.

These statistical tools are applicable to all manner of data. A set of data that can be easily determined, and that is highly informative regarding detection of individuals with clinically significant responsiveness to therapy is provided.

The analysis and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data can be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer can be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

Therapeutic Agents

In one embodiment of the invention, the responsiveness of the individual to therapy is used to guide treatment, where a responsive individual is accordingly treated be maintained in IFNβ therapy, and an unresponsive individual is treated with an alternative or combination regimen.

In various embodiments the therapeutic agent is a biological, e.g. a cytokine, antibody, soluble cytokine receptor, anti-sense oligonucleotide, siRNA, etc. Such biological agents encompass muteins and derivatives of the biological agent, which derivatives can include, for example, fusion proteins, pegylated derivatives, cholesterol conjugated derivatives, and the like as known in the art. Also included are antagonists of cytokines and cytokine receptors, e.g. traps and monoclonal antagonists, e.g. IL-1 Ra, IL-1 Trap, sIL-4Ra, etc. Also included are biosimilar or bioequivalent drugs to the active agents set forth herein.

The method also provide for combination therapy, where the combination can provide for additive or synergistic benefits. Combinations of agents can be obtained with a second agent selected from one or more of the general classes of drugs commonly used in the treatment of the disease of interest, for example including corticosteroids and disease modifying drugs, antigen-specific agents, etc. Corticosteroids have a short onset of action, but many disease modifying drugs take several weeks or months to demonstrate a clinical effect. These agents include methotrexate, leflunomide (Arava™), etanercept (Enbrel™) infliximab (Remicade™), adalimumab (Humira™), anakinra (Kineret™), rituximab (Rituxan™) CTLA4-Ig (abatacept), antimalarials, gold salts, sulfasalazine, d-penicillamine, cyclosporin A, cyclophosphamide azathioprine; and the like. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

In some embodiments of the invention the therapeutic agent is a beta-interferon, including without limitation the currently approved drugs AVONEX™ (IFNβ 1A), BETA-SERON™ (IFN-β1B); EXTAVIA™ (IFN-β1B), REBIF™ (IFNβ 1A), and bioequivalents and derivatives, e.g. pegylated derivatives, thereof. Conditions that can be treated with β-interferons include MS, EAE, etc. Such diseases can also be treated with glatiramer acetate (Copaxone).

In some embodiments of the invention the therapeutic agent is a cytokine or an antagonist, agonist, mimetic, bioequivalent, or derivative thereof. Cytokines of interest include, without limitation, IL-1β; IL-2; IL-4; IL-5; IL-6; IL-7; IL-8; IL-10; IL-11; IL-12; IL-13; IL-15; IL-17 (including IL-17A, B, C, D, E, F separately and in combination, such as IL-17A/F); IL-18; IL-20; IL-21; IL-23; and IL29.

Antagonists of interleukins which can be soluble receptors, antibodies, small molecule drugs, etc. include, without limitation, anti-IL-1, e.g. canakinumab, anakinra, rilonacept, AMG108, XOMA052; anti-IL-4, AMG317; anti-IL-5, mepolizumab, reslizumab, SCH55700, MEDI-563 (receptor); anti-IL6, siltuximab, tocilizumab (receptor), CNTO 136; anti-IL-8, ABX-IL8; anti-IL-9, MEDI-528; anti-IL-12 and IL-23, ustekinumab, briakinumab; anti-IL-13, CAT-354, QAX576; anti-IL-15, AMG 714; anti-IL-17, AIN457, LY2439821, NI-1401; anti-IL-18, GSK1070806; anti-IL-20, NNC109-0012; anti-IL-22, fezakinumab; anti-IL-23, LY2525623. STA-5326 (also called apilimod) is a small molecule inhibitor of IL-12/23 function. LY2439821 and secukinumab (AIN457) are examples of anti-IL-17 monoclonal antibodies.

Antagonists of cytokines include antagonists of IFNα (anti-IFNα); IFNβ (anti-IFNβ); IFNγ (anti-IFNγ); G-CSF (anti-G-CSF); GM-CSF (anti-GM-CSF); Groα (anti-Groα); etc. Agonists of TNFα (anti TNFα), e.g. Enbrel (etanercept), Arcalyst (rilonacept), Amevive (alefacept), find use, for example in the treatment of rheumatic diseases. As used herein, rheumatic diseases can include Ankylosing Spondylitis, Gout, Rheumatoid Arthritis, acute and subacute Bursitis, Kawasaki Syndrome, Relapsing Polychondritis, Bursitis and Tendinitis, Juvenile Idiopathic Arthritis (Juvenile Rheumatoid Arthritis), Sjogren's Syndrome, Cryopyrin-associated Periodic Syndromes, Osteoarthritis, Systemic Sclerosis, Dermatomyositis, Polymyalgia Rheumaticia, Systemic Lupus Erythematous, Epicondylitis, Polymyositis, acute non-specific Tenosynovitis, Fibromyalgia, Psoriatic Arthritis and Vasculitis. Therapies known for rheumatic diseases also include Abatacept (Orencia); Adalimumab (Humira); Anakinra (Kineret); Aspirin (Ecotrin); Auranofin (Ridura); Aurothioglucose (Solganal); Azathioprine (Imuran); Celecoxib (Celebrex); Cyclosporin (Neoral); Etanercept (Enbrel); Gold sodium thiomalate (Myochrysine); Hydroxychloroquine Sulfate (Plaquenil); Infliximab (Remicade); Intravenous Immunoglobulin (Gammagard S/D); Leflunomide (Arava); Methylprednisolone acetate (Depo-Medrol); Methotrexate (Rheumatrex, Trexall); Penicillamine (Cuprimine); Prednisolone (Prednisone (Corticosteroids); Rilonacept (Arcalyst); Rituximab (Rituxan); Sulfasalazine (Azulfidine (Azulfidine EN-Tabs); Triamcinolone acetonide (Kenalog); Triamcinolone diacetate (Aristospan); Diclofenac (Voltaren (Cataflam (Arthrotec (combined with misoprostol)); Diflunisal (Dolobid); Etodolac (Lodine (Lodine XL); Fenoprofen (Nalfon (Nalfon 200); Flurbiprofen (Ansaid); Ibuprofen (Motrin, Tab-Profen, Vicoprofen, combined with hydrocodone) (Combunox, combined with oxycodone); Ibuprofen (Children's Advil); Indomethacin (Indocin, Indocin SR, Indo-Lemmon); Ketoprofen (Oruvail, Orudis); Meloxicam (Mobic); Nabumetone (Relafen); Naproxen (Naprosyn, Anaprox, Anaprox DS, EC-Naprosyn, Naprelan); Oxaprozin (Daypro); Piroxicam (Feldene); Sulindac (Clinoril); Tolmetin (Tolectin, Tolectin DS, Tolectin 600).

Agents that have been found useful in treating inflammatory diseases also include statins, e.g. pravastatin, simvastatin, lovastatin, fluvastatin, atorvistatin, pitavastatin, rosuvastatin, etc.

Other therapeutic agents of interest include lenalidomide (Revlimid); fingolimod (Gilenya); teriflunomide; cladribine; and BG-12 (Panaclar, BG-00012, FAG-201); JAK inhibitors and Syk inhibitors, which include without limitation the JAK-3 inhibitor tasocitinib (CP-690,550); Syk inhibitor fostamatinib (R788) etc.

The compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of compositions of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Treating, treatment, or therapy of a disease or disorder shall mean slowing, stopping or reversing the disease's progression by administration of treatment according to the present invention. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration of a composition to prevent the occurrence or onset of a disease or disorder or some or all of the symptoms of a disease or disorder or to lessen the likelihood of the onset of a disease or disorder.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

EXAMPLE 1

Analysis of B Cell Subsets in Multiple Sclerosis Patients on Immunomodulatory Therapy Reveals Modulation of $CD19^+CD24^{hi}CD38^{hi}$ Cells with Implications for the Diagnosis and Monitoring of MS Objective: To define serum levels of B-cell activation factor (BAFF) and specific B-cell phenotypes in remitting multiple sclerosis (RRMS) patients treated with either glatiramer acetate (GA) or interferon-$\beta$ (IFN$\beta$). To determine whether B cells are necessary for effective treatment with IFN$\beta$ in experimental autoimmune encephalomyelitis (EAE).

Background: There are currently no serologic tests that aid in the selection or monitoring of therapy in RRMS. The role of B-cells in RRMS remains unclear.

Design/Methods: We recruited 13 patients (IFN$\beta$=7, GA=6) from the Stanford MS Center who met the following criteria: 1) age 20-45, 2) diagnosis of RRMS for less than 7 years, 3) clinically stable at the time of blood draw. We conducted ELISA for plasma BAFF levels and FACS for B-cell subsets. In EAE, we assessed BAFF levels, B-cell phenotypes, and disease in wild-type (WT) and muMT (B-cell deficient) mice treated with IFN$\beta$.

Results: In patients, there was a trend towards increased BAFF in serum in patients treated with IFN$\beta$ compared to GA. There was a significant increase in circulating B-cells ($p<0.005$) and $CD24^{hi}CD38^{hi}$ transitional B-cells ($p<0.001$) in IFN$\beta$ compared to GA. In EAE mice, rmIFN$\beta$ treatment significantly increase in $CD19_+$ B cells (n=3, $p<0.05$) and serum BAFF levels (n=5, p=0.003) in IFN$\beta$ compared to PBS controls. muMT mice developed EAE, but in contrast to WT animals did not respond to IFN$\beta$ (n=3 per group).

Conclusions: These data demonstrate one effect of IFN$\beta$ therapy is expanding transitional B-cells populations, which may have regulatory effects in MS. The importance of B-cells was confirmed in EAE, where B-cells are necessary for successful IFN$\beta$ therapy. This study has implications for the monitoring and treatment of RRMS patients.

PBMS Isolation and FACS analysis. Peripheral blood mononuclear cells (PBMC) were isolated from the peripheral blood of donors using a ficoll gradient. Plasma was separated at the isolation step and stored at −80 degrees celsius. The buffy coat was washed and stored overnight at −80° C. in 90% autologous plasma and 10% DMSO before transfer to −180° C. for longer term storage. For FACS analysis, cells were removed from cryopreservation and rapidly warmed to 37° C. prior to surface marker staining. Antibodies used were CD38-PE, CD19-perCP-Cy5.5, CD24-FITC. CD38-CD1d, CD5-fitc, and CD27-FITC (all purchased from eBiosciences). Data was acquired using the FACS scan (Becton Dickinson) and analyzed using FlowJo (Tree Star). Statistical analyses were performed using GraphPad Prism (GraphPad Software).

| CRITERIA | IFN$\beta$ | COPAXONE | HEALTHY Control |
|---|---|---|---|
| Number of Patients | 6 | 13 | 3 |
| Age | 37.2 | 37.2 | 28.7 |
|  | Range: 24-44 | Range: 26-46 | Range: 24-36 |

| CRITERIA | IFNβ | COPAXONE | HEALTHY Control |
|---|---|---|---|
| Gender | 5F, 1M | 10F, 3M | 3M |
| Diagnosis | RRMS | RRMS | N/A |
| Years since Diagnosis | 5.8 Range: 1-8 | 4.2 Range: 1-8 | 0 |
| EDSS | 1.3 Range: 0-2.5 | 1.5 Range: 0-4 | 0 |
| BAFF level (pg/ml) | 853.5 Range: 536-1122 | 691.9 Range: 622-780 | 696.7 Range: 604-785 |
| Total B cells (% of all gated lymphocytes) | 10.6 Range: 7.4-12.8 | 8.1 Range: 6.2-11.6 | 9.0 Range: 7.4-12 |
| Transitional B cells (% of CD19+) | 12.4 Range: 7.4-17.3 | 2.5 Range: 0.5-5.2 | 2.6 Range: 2.1-2.9 |

Transitional B cells appears uniquely expanded in RRMS patients on IFNβ therapy but not in GA and these cells are a more reliable biomarker of treatment than serum BAFF, demonstrating their utility in treatment monitoring.

IFNβ treatment expands transitional B cells through a mechanism dependent upon the presence of BAFF. The addition of IFNβ to conditions mimicking B cell activation stimulates the production of IL-10, IL-6, and IFNγ. IL-10 has well-documented anti-inflammatory effects, and may be a critical link between B cells and the successful treatment of RRMS with IFNβ. In EAE, IFNβ preferentially expands marginal zone B cells in the spleen. Treatment of EAE with IFNβ requires the presence of B cells. Taken together, these data provide direct evidence for the regulatory effect of IFNβ through marginal zone B cell stimulation.

What is claimed is:

1. A method of treating an individual with multiple sclerosis, the method comprising:
   obtaining a hematopoietic cell sample from a patient having multiple sclerosis (MS), wherein the patient has been previously treated with interferon beta (IFNβ);
   determining the number of $CD19_+$, $CD24_+$, $CD38_+$ transitional B cells in the hematopoietic cell sample;
   treating the MS patient with IFNβ when the patient has an increased number of $CD19_+$, $CD24_+$, $CD38_+$ transitional B cells relative to an untreated or unresponsive MS control sample, wherein the patient is determined to be responsive to IFNβ;and
   treating the MS patient with a therapeutic agent other than IFNβ when the patient does not have an increasd number of $CD19_+$, $CD24_+$, $CD38_+$ transitional B cells relative to an untreated or unresponsive MS control sample.

2. The method of claim 1, wherein the individual is undergoing treatment with the IFNβ agent.

3. The method of claim 1, wherein the patient is undergoing treatment with a therapeutic agent that mimics IFNβ.

4. The method of claim 1, wherein the determining step comprises:
   combining reagents that specifically recognize at least one of CD19, CD24 and CD38 transitional B cell markers with the sample comprising hematopoietic cells; and
   enumerating those cells that are positive for expression of at least one of CD19, CD24 and CD38.

5. The method of claim 4, further comprising
   and IgM with the sample comprising hematopoietic cells; and
   enumerating those cells that are positive for expression of IgD or IgM.

6. The method of claim 5, wherein the determining step is performed by flow cytometry.

7. The method of claim 5, wherein the individual is human.

8. A method of treating an individual with multiple sclerosis, the method comprising:
   treating a multiple sclerosis (MS) patient with a therapeutic agent;
   obtaining a hematopoietic cell sample from the patient;
   determining the number of $CD19_+$, $CD24_+$, $CD38_+$ transitional B cells in the hematopoietic cell sample; and
   continuing treatment of the MS patient with the therapeutic agent when the patient has an increased number of $CD19_+$, $CD24_+$, $CD38_+$ transitional B cells relative to an untreated or unresponsive MS control sample, wherein the patient is determined to be responsive to the therapeutic agent.

* * * * *